(12) United States Patent
Kaluzny et al.

(10) Patent No.: US 11,219,383 B2
(45) Date of Patent: Jan. 11, 2022

(54) RADIOFREQUENCY DETECTION AND IDENTIFICATION OF PRESSURE SENSING CATHETERS

(71) Applicant: Laborie Medical Technologies Corp., Williston, VT (US)

(72) Inventors: Michael Kaluzny, Toronto (CA); Adrian G. Dacko, Mississauga (CA); Marato Gebremichael, Toronto (CA); David Nathaniel Cole, Brampton (CA); Christopher Driver, Oakville (CA)

(73) Assignee: Laborie Medical Technologies Corp., Portsmouth, NH (US)

( * ) Notice: Subject to any disclaimer, the term of this patent is extended or adjusted under 35 U.S.C. 154(b) by 0 days.

(21) Appl. No.: 16/258,966

(22) Filed: Jan. 28, 2019

(65) Prior Publication Data
US 2020/0237242 A1    Jul. 30, 2020

(51) Int. Cl.
*A61B 5/03*    (2006.01)
*H01Q 1/24*    (2006.01)
*A61B 90/00*    (2016.01)

(52) U.S. Cl.
CPC .............. *A61B 5/036* (2013.01); *A61B 90/39* (2016.02); *H01Q 1/246* (2013.01);
(Continued)

(58) Field of Classification Search
CPC ... A61B 5/036; A61B 90/39; A61B 2090/392; A61B 2090/0807; A61B 2562/0247; H01Q 1/246
See application file for complete search history.

(56) References Cited

U.S. PATENT DOCUMENTS

| 4,752,292 A | 6/1988 | Lopez et al. |
| 5,135,484 A | 8/1992 | Wright |

(Continued)

FOREIGN PATENT DOCUMENTS

| CN | 1859942 A | 11/2006 |
| EP | 774919 B1 | 11/2002 |

(Continued)

OTHER PUBLICATIONS

Smith et al., U.S. Appl. No. 16/045,895, filed Jul. 26, 2018, entitled "Pressure Catheter Connector," 45 pages.
(Continued)

*Primary Examiner* — Rene T Towa
(74) *Attorney, Agent, or Firm* — Fredrikson & Byron, P.A.

(57) ABSTRACT

A charger for charging a plurality of pressure sensing catheters is provided. The charger has a plurality of charging ports of which a first charging port and a second charging port receives a first connector and a second connector respectively. The first and second connectors each have a first and second radiofrequency identification tags respectively, having information indicative of identifiable information of a first and second pressure sensing catheters respectively. The charger has a plurality of antennas, of which a first antenna and a second antenna can be positioned proximate to the first charging port, and second charging port respectively. When the first connector is inserted into the first charging port, the first radiofrequency identification tag is guided to a predetermined orientation with respect to the first antenna to minimize a spacing therebetween, and to maximize absorption of radiofrequency energy therebetween.

29 Claims, 5 Drawing Sheets

(52) U.S. Cl.
CPC . *A61B 2090/0807* (2016.02); *A61B 2090/392* (2016.02); *A61B 2562/0247* (2013.01)

(56) References Cited

U.S. PATENT DOCUMENTS

| | | | |
|---|---|---|---|
| 5,573,007 | A | 11/1996 | Bobo |
| 5,776,116 | A * | 7/1998 | Lopez ............... A61M 39/1011 604/244 |
| 5,795,325 | A | 8/1998 | Valley et al. |
| 6,421,013 | B1 * | 7/2002 | Chung ............ G06K 19/07749 343/700 MS |
| 6,649,829 | B2 | 11/2003 | Garber et al. |
| 6,673,022 | B1 | 1/2004 | Bobo et al. |
| 6,837,864 | B1 | 1/2005 | Bertolero et al. |
| 7,352,771 | B2 | 4/2008 | Garber |
| 7,926,856 | B2 | 4/2011 | Smutney et al. |
| RE44,310 | E | 6/2013 | Chadbourne et al. |
| 2004/0127813 | A1 | 7/2004 | Schwamm |
| 2005/0064223 | A1 | 3/2005 | Bavaro et al. |
| 2005/0187430 | A1 | 8/2005 | Aundal et al. |
| 2005/0215119 | A1 * | 9/2005 | Kaneko ............... H01R 9/2475 439/607.01 |
| 2006/0148279 | A1 * | 7/2006 | German ............... H01R 29/00 439/49 |
| 2007/0073270 | A1 | 3/2007 | Christensen |
| 2007/0252771 | A1 | 11/2007 | Maezawa et al. |
| 2007/0273525 | A1 | 11/2007 | Garber et al. |
| 2008/0030343 | A1 * | 2/2008 | Raybuck ............... A61B 90/90 340/572.8 |
| 2008/0143480 | A1 * | 6/2008 | Egbert ............... H04B 5/0062 340/10.1 |
| 2009/0009290 | A1 * | 1/2009 | Kneip ............... A61M 1/28 340/10.1 |
| 2009/0171278 | A1 | 7/2009 | Hirszowicz et al. |
| 2009/0306539 | A1 | 12/2009 | Woodruff et al. |
| 2010/0001516 | A1 | 1/2010 | Pisula, Jr. et al. |
| 2010/0249663 | A1 | 9/2010 | Nishtala |
| 2010/0249723 | A1 | 9/2010 | Fangrow, Jr. |
| 2010/0280451 | A1 | 11/2010 | Teeslink et al. |
| 2011/0136550 | A1 | 6/2011 | Maugars |
| 2011/0152841 | A1 | 6/2011 | Nemoto |
| 2011/0210541 | A1 | 9/2011 | Lewis et al. |
| 2013/0015654 | A1 | 1/2013 | Gilham et al. |
| 2013/0184612 | A1 | 7/2013 | Quackenbush et al. |
| 2013/0268029 | A1 * | 10/2013 | Cauller ............... A61B 5/6849 607/61 |
| 2013/0270820 | A1 | 10/2013 | Py |
| 2014/0203077 | A1 | 7/2014 | Gadh et al. |
| 2014/0266775 | A1 | 9/2014 | Moon et al. |
| 2015/0130408 | A1 | 5/2015 | Wei |
| 2015/0135502 | A1 | 5/2015 | Rankin et al. |
| 2015/0250974 | A1 | 9/2015 | Bobo, Sr. et al. |
| 2016/0029912 | A1 * | 2/2016 | Stimpson ............ A61B 5/6852 600/561 |
| 2016/0046130 | A1 | 2/2016 | Burdge et al. |
| 2016/0089254 | A1 | 3/2016 | Hopkinson et al. |
| 2016/0213228 | A1 | 7/2016 | Rohl et al. |
| 2016/0274311 | A1 * | 9/2016 | Verheyden ............ G02B 6/3879 |
| 2017/0021144 | A1 | 1/2017 | Kanner et al. |
| 2017/0140330 | A1 | 5/2017 | Rinzler et al. |
| 2017/0209682 | A1 | 7/2017 | Shemesh |
| 2017/0258345 | A1 | 9/2017 | Smith |
| 2017/0259035 | A1 | 9/2017 | Smith et al. |

FOREIGN PATENT DOCUMENTS

| | | |
|---|---|---|
| EP | 1996851 B1 | 11/2011 |
| EP | 1799610 B1 | 11/2012 |
| EP | 1866611 B1 | 9/2014 |
| EP | 2837403 A1 | 2/2015 |
| EP | 3219353 A1 | 9/2017 |
| EP | 3332834 A1 | 6/2018 |
| WO | 2005032639 A1 | 4/2005 |
| WO | 2005107006 A1 | 11/2005 |
| WO | 2009055435 A1 | 4/2009 |

OTHER PUBLICATIONS

Smith et al., U.S. Appl. No. 16/046,061, filed Jul. 26, 2018, entitled "Charger for Pressure Sensing Catheter," 49 pages.
Smith et al., Design U.S. Appl. No. 29/657,875, filed Jul. 26, 2018, entitled "Pressure Catheter Connector," 11 pages.
International Patent Application No. PCT/US2019/043191, International Search Report dated Feb. 20, 2020, 7 pages.
English Abstract for Chinese Publication No. CN 1859942 A, published Nov. 8, 2006, 1 pgs.
International Patent Application No. PCT/US2020/015428, International Search Report and Written Opinion dated Jul. 7, 2020, 23 pages.

* cited by examiner

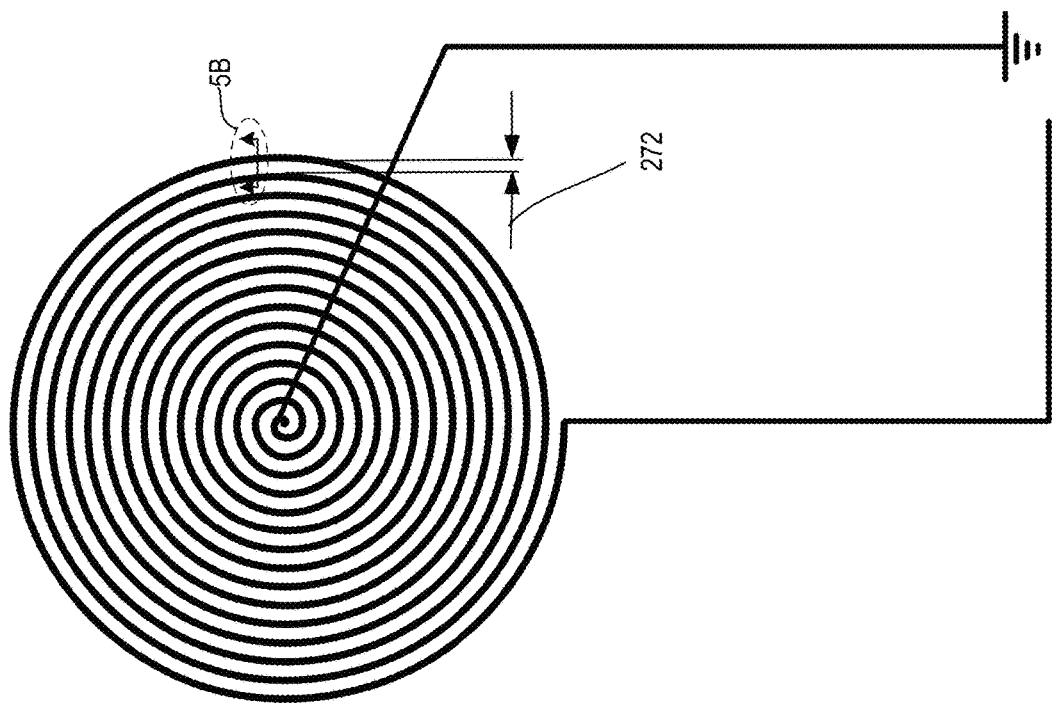
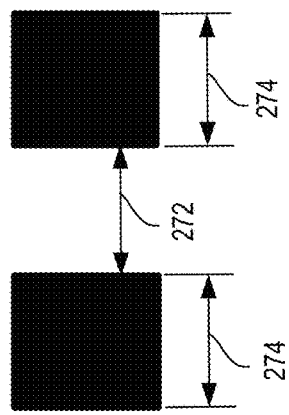
Fig. 5B
Fig. 5A

US 11,219,383 B2

RADIOFREQUENCY DETECTION AND IDENTIFICATION OF PRESSURE SENSING CATHETERS

BACKGROUND

Pressure catheter devices can be used for the measurement and analysis of pressure within a body cavity. Such devices typically include an elongate catheter having at least one gas-filled pressure monitoring lumen extending longitudinally through the catheter. A gas-filled membrane (e.g., a balloon) can be formed on the outer surface of the catheter. The gas-filled membrane can be in fluid communication with the gas-filled pressure monitoring lumen. Changes in pressure against the gas-filled membrane may result in changes in pressure of the gas within the gas-filled pressure monitoring lumen. A pressure transducer connected to the proximal end of the gas-filled pressure monitoring lumen can sense and display or record the changes in pressure which can be communicated through the gas-filled pressure monitoring lumen of the catheter.

Some such pressure catheters may be connected by connectors to permit charging the gas-filled membrane. For instance, engagement of connectors may displace a volume of fluid and thereby charge the gas-filled membrane. Such catheters and connectors are described in commonly-assigned patent applications, U.S. 2017/0259035 A1 and U.S. 2017/0258345 A1, the entire contents of which is hereby incorporated by reference.

In several conventional pressure catheter and charger systems, the catheter may be a disposable component that may be disposed after a single use, while a charger may be a multi-use component. Additionally, in some cases, the catheter may be reused for a particular patient and stored between uses. Further, in some cases, a single type of charger may be used for charging several types of catheters. However, many conventional pressure catheter and charger systems do not include any components to detect and identify details of a particular pressure catheter connected to the charger. In some cases, not recognizing an unsuitable type of catheter for a particular procedure (e.g., a urodynamic catheter for an anorectal measurement), or a previously-used catheter may be undesirable. Further, providing components in the charger or connector that include wired electrical connections to detect and identify a catheter may be disfavored and may, in some cases, be non-compliant with safety regulations for such devices.

SUMMARY

In one aspect, the present disclosure provides a charger for charging a plurality of pressure sensing catheters. The charger may have a plurality of charging ports of which a first charging port may receive a first connector of a first pressure sensing catheter of the plurality of pressure sensing catheters. The first connector can have a first radiofrequency identification tag that has information that is indicative of identifiable information of the first pressure sensing catheter. A second charging port of the plurality of charging ports can receive a second connector of a second pressure sensing catheter of the plurality of pressure sensing catheters. The second connector can have a second radiofrequency identification tag that has information that is indicative of identifiable information of the second pressure sensing catheter. The charger can have a plurality of antennas, of which a first antenna and a second antenna can be adjacent to and be generally coplanar with each other on a common plane. The first antenna can be positioned proximate to the first charging port, and the second antenna can be positioned proximate to the second charging port, such that a spacing between the first radiofrequency identification tag and the first antenna is less than: (a) a first distance between the first antenna and the second antenna, or (b) second distance between the first radiofrequency identification tag and the second radiofrequency identification tag, or (c) a third distance between the first radiofrequency identification tag and the second antenna. Each of the first antenna and the second antenna can have a thickness and a diameter. The thickness can be substantially less than the diameter, such that each of the first antenna and the second antenna emits or receives radiofrequency energy in a direction generally perpendicular to the common plane, such that radiofrequency communication between the first radiofrequency tag and the second antenna is minimized.

In another aspect, a pressure sensing system can include a first connector connectable to a first pressure sensing catheter comprising one or more balloons. The first connector can have a handle for grasping and orienting the first connector, a tag housing spaced apart from the handle, and a first radiofrequency identification tag positioned within the tag housing. The first radiofrequency identification tag can have information for identifying the first pressure sensing catheter. The pressure sensing system can include a charger for charging the one or more balloons of the pressure sensing catheter pressure sensing catheter. The charger can have a first charging port for receiving the connector, and a first antenna positioned proximal to the first charging port. The first antenna can read the information stored on the first radiofrequency identification tag when the first radiofrequency identification tag is within a range of the first antenna. When the first connector is inserted into the first charging port, the first radiofrequency identification tag is guided to a predetermined orientation with respect to the first antenna. The predetermined orientation can minimize a spacing between the first antenna and the first radiofrequency identification tag when the connector is being inserted into the charging port, so as to maximize absorption of radiofrequency energy emitted by the first radiofrequency identification tag using the first antenna.

Embodiments of the present disclosure also include one or more of the following numbered embodiments:

1. A charger for charging a plurality of pressure sensing catheters, the charger comprising:
    a plurality of charging ports,
    a first charging port of the plurality of charging ports being configured to receive a first connector of a first pressure sensing catheter of the plurality of pressure sensing catheters, the first connector having a first radiofrequency identification tag that has information that is indicative of identifiable information of the first pressure sensing catheter,
    a second charging port of the plurality of charging ports being configured to receive a second connector of a second pressure sensing catheter of the plurality of pressure sensing catheters, the second connector having a second radiofrequency identification tag that has information that is indicative of identifiable information of the second pressure sensing catheter;
    a plurality of antennas comprising a first antenna and a second antenna, the second antenna being adjacent to and generally coplanar with the first antenna on a common plane, the first antenna being positioned proximate to the first charging port, and the second antenna being positioned proximate to the second charging port, such that:

a spacing between the first radiofrequency identification tag and the first antenna is less than a first distance between the first antenna and the second antenna, or the spacing between the first radiofrequency identification tag and the first antenna being less than a second distance between the first radiofrequency identification tag and the second radiofrequency identification tag, or the spacing between the first radiofrequency identification tag and the first antenna being less than a third distance between the first radiofrequency identification tag and the second antenna, each of the first antenna and the second antenna having a thickness and a diameter, the thickness being substantially less than the diameter, such that each of the first antenna and the second antenna emits or receives radiofrequency energy in a direction generally perpendicular to the common plane, such that radiofrequency communication between the first radiofrequency tag and the second antenna is minimized.

2. The charger of embodiment 1 or any previous embodiment, further comprising a printed circuit board, wherein each antenna is a spiral antenna formed on the printed circuit board, the spiral antenna being configured to emit radiofrequency energy in a direction generally perpendicular to a plane of the printed circuit board.

3. The charger of embodiment 2 or any previous embodiment, further comprising a plurality of grounding pads, each grounding pad being positioned between two adjacent antennas, the grounding pads configured to absorb radiofrequency energy emitted by each antenna in a direction parallel to the plane of the printed circuit board.

4. The charger of embodiment 2 or any previous embodiment, wherein the spiral antenna has a spiral diameter of between about 2 millimeters and about 10 millimeters.

5. The charger of embodiment 2 or any previous embodiment, wherein the spiral antenna comprises a conductor wound in spirals, a width of the conductor forming the spiral antenna between about 0.05 millimeters and about 0.2 millimeters.

6. The charger of embodiment 2 or any previous embodiment, wherein the spiral antenna has between about 15 spirals and about 25 spirals.

7. The charger of embodiment 1 or any previous embodiment, wherein each antenna is configured to have a resonant frequency that matches a frequency of transmission of the radiofrequency identification tag.

8. The charger of embodiment 1 or any previous embodiment, further comprising a radiofrequency identification processor configured to receive, via one or more antennas of the plurality of antennas, information stored on the radiofrequency identification tag, the radiofrequency identification processor being configured to identifying the pressure sensing catheter.

9. The charger of embodiment 8 or any previous embodiment, wherein the radiofrequency identification processor being configured to determine, based on the information received from the radiofrequency identification tag, whether the pressure sensing catheter received in the corresponding charging port is a correct type catheter for a predetermined measurement procedure.

10. The charger of embodiment 8 or any previous embodiment, further comprising a multiplexer operatively coupled to the plurality of antennas, the multiplexer being in operative communication with the radiofrequency identification processor.

11. The charger of embodiment 10 or any previous embodiment, wherein the radiofrequency identification processor is configured to communicate with the multiplexer so as to read information transmitted via the plurality of antennas according to a predetermined sequence.

12. The charger of embodiment 10 or any previous embodiment, wherein each antenna is electrically connected to the multiplexer by a transmission line, the transmission line having an impedance that equals an impedance of the antenna.

13. A pressure sensing system, comprising:

a first connector connectable to a first pressure sensing catheter comprising one or more balloons, the first connector having:

a handle for grasping and orienting the first connector, a tag housing spaced apart from the handle, a first radiofrequency identification tag positioned within the tag housing, the first radiofrequency identification tag having information for identifying the first pressure sensing catheter;

a charger for charging the one or more balloons of the pressure sensing catheter pressure sensing catheter, the charger comprising:

a first charging port for receiving the connector, and a first antenna positioned proximal to the first charging port, the first antenna being configured to read the information stored on the first radiofrequency identification tag when the first radiofrequency identification tag is within a range of the first antenna, whereby when the first connector is inserted into the first charging port, the first radiofrequency identification tag is guided to a predetermined orientation with respect to the first antenna, the predetermined orientation minimizing a spacing between the first antenna and the first radiofrequency identification tag when the connector is being inserted into the charging port, so as to maximize absorption of radiofrequency energy emitted by the first radiofrequency identification tag using the first antenna.

14. The pressure sensing system of embodiment 13 or any previous embodiment, wherein the first radiofrequency identification tag is brought within the range of the first antenna before the first connector is fully inserted into the charging port.

15. The pressure sensing system of embodiment 14 or any previous embodiment, wherein the spacing between the first radiofrequency identification tag and the first antenna is such that radiofrequency energy radiated by the first radiofrequency identification tag and/or the first antenna is generally oriented toward each other.

16. The pressure sensing system of embodiment 15 or any previous embodiment, wherein the distance between the first radiofrequency identification tag and the first antenna is between about 2 millimeters and about 10 millimeters, so as to increase absorption of radiofrequency energy emitted by the first radiofrequency identification tag using the first antenna.

17. The pressure sensing system of embodiment 13 or any previous embodiment, wherein when at the predetermined orientation, the first antenna and the first radiofrequency identification tag are generally parallel to each other.
18. The pressure sensing system of embodiment 13 or any previous embodiment, wherein when at the predetermined orientation, a center of the first radiofrequency identification tag and a center of the first antenna each generally lie on the same line.
19. The pressure sensing system of embodiment 13 or any previous embodiment, further comprising:
a second connector connectable to a second pressure sensing catheter, the second connector having a second radiofrequency identification tag positioned thereon, the second radiofrequency identification tag having information for identifying the second pressure sensing catheter;
a second charging port for receiving the second connector; and
a second antenna configured to read the information stored on the second radiofrequency identification tag, when the second radiofrequency identification tag is within a range of the second antenna.
20. The pressure sensing system of embodiment 19 or any previous embodiment, wherein a first spacing between the first radiofrequency identification tag and the first antenna is less than a first distance between the first antenna and the second antenna.
21. The pressure sensing system of embodiment 20 or any previous embodiment, wherein the first spacing between the first radiofrequency identification tag and the first antenna is less than a second distance between the first radiofrequency identification tag and the second radiofrequency identification tag.
22. The pressure sensing system of embodiment 21 or any previous embodiment, the first spacing between the first radiofrequency identification tag and the first antenna is less than a third distance between the first radiofrequency identification tag and the second antenna.
23. The pressure sensing system of embodiment 1 or any previous embodiment, wherein the spacing between the first radiofrequency identification tag and the first antenna being less than a distance between the first antenna and any antenna of the plurality of antennas other than the first antenna.
24. The pressure sensing system of embodiment 1 or any previous embodiment, wherein the common plane is a plane defined by a portion of each antenna of the plurality of antennas.
25. The pressure sensing system of embodiment 24 or any previous embodiment, wherein each antenna of the plurality of antennas lie in the common plane.
26. The pressure sensing system of embodiment 13 or any previous embodiment, wherein the handle comprises a first end portion configured to be depressed so as to provide torque to engage the first connector with the first charging port.
27. The pressure sensing system of embodiment 26 or any previous embodiment, wherein the handle comprises a second end portion configured to be grasped to guide and insert the connector into the charging port.
28. The pressure sensing system of embodiment 27 or any previous embodiment, wherein the tag housing is spaced the first end portion or the second end portion.

BRIEF DESCRIPTION OF DRAWINGS

FIG. 5A is an enlarged view of an antenna illustrated in FIG. 4
FIG. 5B is a cross-sectional view of the portion 5B of the antenna illustrated in FIG. 5A.

DETAILED DESCRIPTION

For purposes of illustrating the various aspects of the methods and systems claimed herein, the discussion below will be directed to describing exemplary embodiments used in anatomical pressure sensing catheter 10 associated connectors, charger (which includes one or more charging ports) and a measurement system. The elements and principles discussed herein are applicable to applications such as urodynamic, esophageal, anorectal manometry, and the like. Further, the exemplary embodiments described herein are contemplated for use with any type of catheter 10 wherein measurement of pressure within the body of a patient is desired. Discussion of methods and systems herein can be interchangeable with respect to specific aspects. In other words, specific discussion of one method or system (or components thereof) herein is equally applicable to other aspects as they relate to the system or method, and vice versa.

Figure 1:
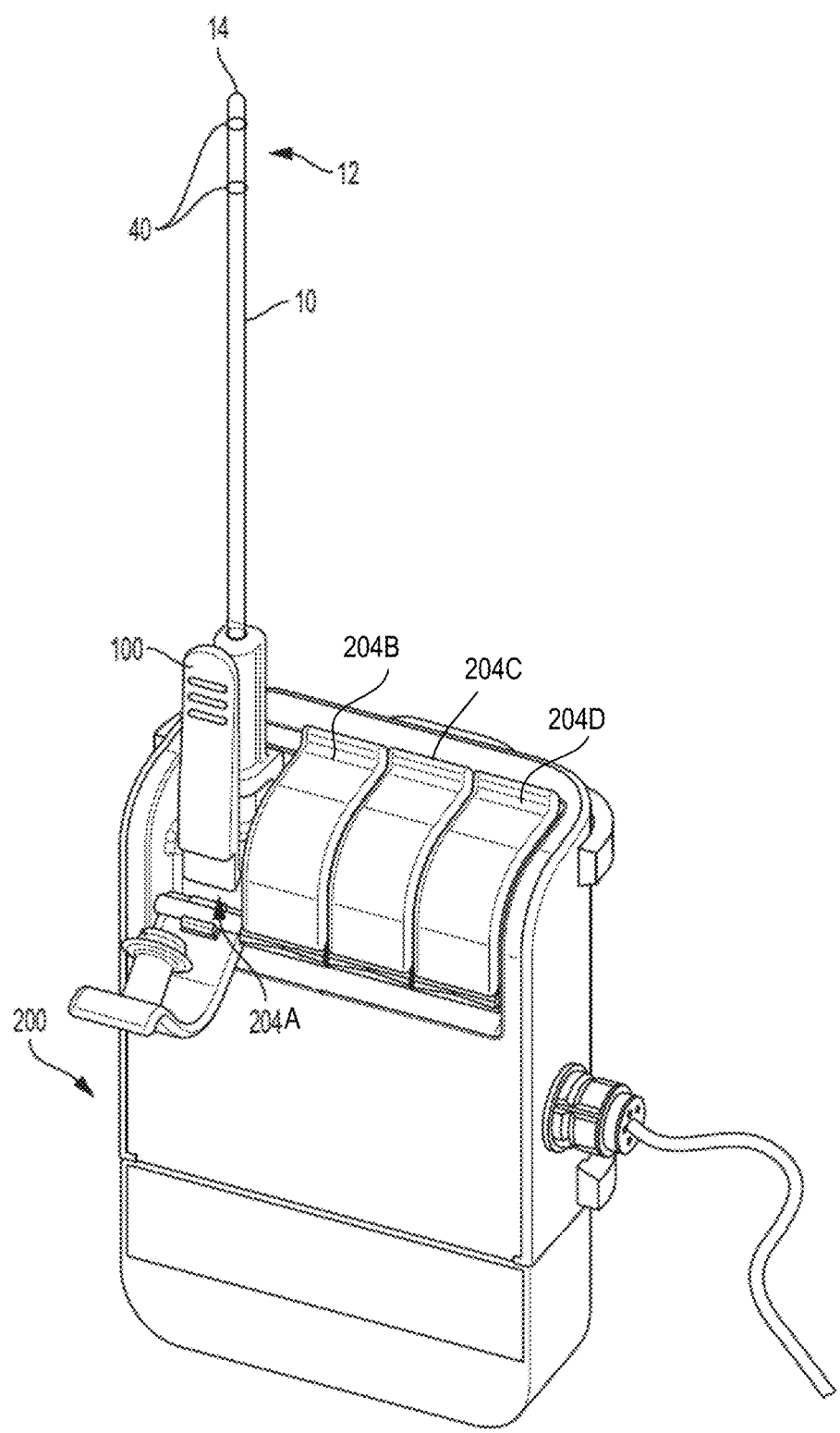
FIG. 1 is a perspective view of an anatomical pressure sensing system according to an embodiment.

FIG. 1 illustrates a pressure catheter 10 and charger system for use in various manometry applications. The pressure sensing catheter 10 comprises a proximal section and a distal section 12. One or more flaccid, pressure-compliant members (e.g., a medical grade balloon 40 or bladder used in medical applications) 40 are located on a distal section 12 of the catheter 10. The balloons 40 are configured to receive a predetermined volume of a pressure transmission medium (e.g., air or other fluids) from within the charger to resist induced pressure forces acting externally on the balloon 40. The induced pressure forces are transmitted via the balloon 40 to the charger. The charger, in turn, may have one or more pressure transducers that permit measurement of the induced pressure forces.

Details of the pressure sensing catheter 10 and/or charger are described in commonly-assigned patent applications, titled, "Pressure Catheter Connector" U.S. Ser. No. 16/045,895 filed on Jul. 26, 2018 and "Charger for Pressure Sensing Catheter," U.S. Ser. No. 16/046,061 filed on Jul. 26, 2018 the entire contents of each of which is hereby incorporated by reference. As disclosed therein, the charger includes one or more charging ports for receiving a proximal connector 100 of the pressure sensing catheter 10. An engagement between the pressure sensing catheter 10 and the proximal connector 100 may result in a volume of pressure transmission medium being displaced from the charging port toward the distal section 12 of the catheter 10 and thereby charge the balloon 40. In the illustrated embodiment, four charging ports are illustrated, however, additional or fewer charging ports are contemplated within the scope of the present disclosure.

The catheter 10 may be a disposable component that may be disposed after a single use, while a charger may be a multi-use component. Alternatively, in certain embodiments, the catheter 10 may not be disposed after a single use, and a particular catheter 10 used with a patient may be reused with that specific patient for a subsequent measurement. Accordingly, systems and methods disclosed herein permit detection and/or identification of a catheter 10 prior to being inserted into a patient. In certain advantageous embodiments, the systems and methods disclosed herein can permit detection and/or identification of a catheter 10 when the proximal connector 100 is inserted into a charging port, and/or prior to being fully engaged with the charging port.

Certain embodiments of the present disclosure provides an electronic tag and/or an antenna 210 combination to permit detection of pressure sensing catheters being connected to a charging port. In some such aspects, the electronic tag and/or antenna 210 can communicate wirelessly by establishing radiofrequency communication therebetween. While embodiments described below describe a radiofrequency identification (hereinafter "RFID") tag and a radiofrequency (hereinafter, "RF") antenna 210, it should be understood that systems and methods described herein may be adapted to other types of wireless communication systems (e.g., Bluetooth, WiFi, etc.) between the pressure sensing catheters and corresponding charging ports engaging therewith.

Figure 2:
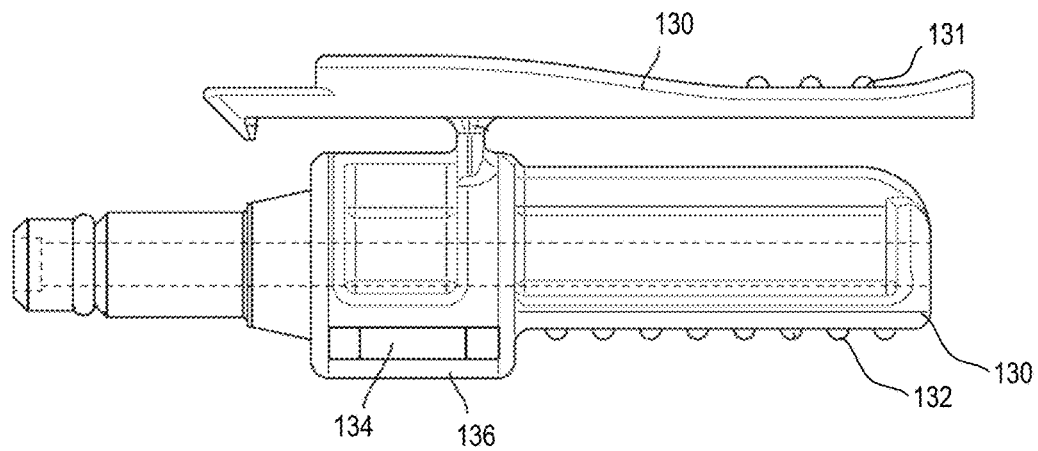
FIG. 2 is a side view of a catheter connector shown in FIG. 1 according to an embodiment.

In an embodiment, the electronic tag can be a RFID tag 134. FIG. 2 illustrates one such connector 100 with the RFID tag 134. In FIG. 2, the connector 100 has a tag housing 136 shaped as a slot, and the RFID tag 134 can be positioned therewith. In some such advantageous embodiments, the connector 100 can be advanced into a charging port of the charger. The connector 100 includes a handle 130 to guide the connector 100 into a charging port of the charger. The handle 130 may have a first end portion 131 that can be depressed (e.g., by a thumb of the operator) to provide a sufficient torque to engage the connector 100 with the charging port. The handle 130 may have a second end portion 132 that may be grasped (e.g., by the fingers of an operator) to guide and insert the connector 100 into the charging port. The tag housing 136, as seen from FIG. 2 is spaced apart from both the first end portion 131 and the second end portion 132. For instance, in the illustrated embodiment, the tag housing 136 is axially spaced apart from the first and second end portions 131, 132.

According to certain embodiments, the handle 130 can, as illustrated, be rotationally keyed so as to insert the connector 100 into the charging port. Alternatively, the charging port and the connector 100 can be at any (rotational) orientation with respect to each other, however, as the connector 100 is inserted, the RFID tag 134 may be guided to be at a predetermined orientation with respect to the antenna 210 so as to permit maximum RF energy absorption between the tag 134 and the antenna 210. The connector 100 may not have to be fully seated in the charging port for the tag 134 to be brought into predetermined orientation with respect to the antenna 210. For example, the antenna 210 may already be at a predetermined orientation and thereby have a direct line of sight of the tag housing 136 at the time of insertion or when a certain fraction (e.g., $\frac{1}{3}^{rd}$, $\frac{3}{4}$, or other fractions) of the connector 100 has been received within the charging port. Alternatively, the connector 100 may be fully inserted in order to have the tag 134 and the antenna 210 to be at a predetermined orientation.

Other components of the connector 100 may be arranged such that RF energy received by the antenna 210 and/or emitted by the tag housing 136 is not blocked. Accordingly, the side of the connector 100 that has the tag housing 136 may be closer to the antenna 210 than the side that has the handle 130. When such an orientation is established, the RFID tag 134 may be read easily. In alternative embodiments, the connector 100 may not have rotational keying, and the RFID tag 134 may be positioned at other locations instead of at the location illustrated in FIG. 2. The RFID tag 134 may, for instance, be wrapped around an exterior of the connector 100.

The RFID tag 134 can store information that may include a unique number that may be indicative of any of the following: catheter 10 type, manufacturer, specifications, whether or not the catheter 10 has been previous used, and the like. The information stored corresponding to the serial number of the RFID tag 134 read by the antenna 210 can be used to determine whether a suitable catheter 10 (e.g., catheter 10 type, size, whether catheter 10 was used previously) coupled to the connector 100 is being used for a particular procedure. In some embodiments, the serial number of the RFID tag 134 can be unique to each catheter 10. As will be described further below, a look-up table may correlate the unique code to information that can be used for identifying the catheter 10.

Figure 3:
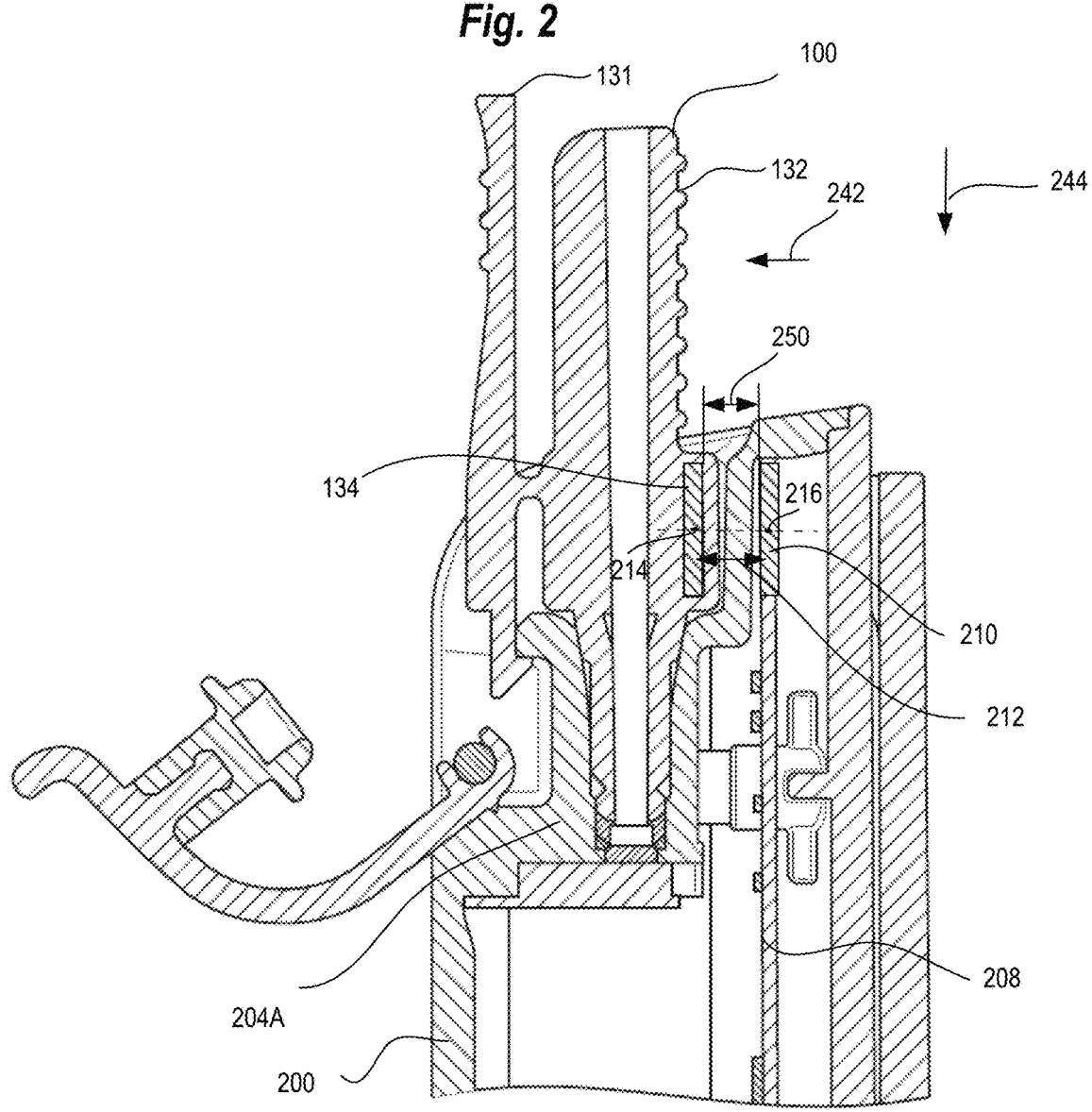
FIG. 3 is a partial section view of the charger of FIG. 1 shown with a connector engaged thereto.

FIG. 3 illustrates a partial sectional view of a charger engaged to a catheter 10 connector 100. As shown in FIG. 3, the charger can include an antenna 210 for reading the information stored corresponding to the serial number of the RFID tag 134. In an embodiment, the antenna 210 can be in operative communication with electronic circuitry provided in the charger that permit electrical communication between various components of the charger. In advantageous embodiments, the electronic circuitry can be in the form of traces on and/or components mounted to a printed circuit board 208.

With continued reference to FIG. 3, when the antenna 210 is at a predetermined orientation with respect to the RFID tag 134, the antenna 210 and the radiofrequency identification tag 134 may be generally parallel to each other. Additionally, or alternatively, when the antenna 210 is at a predetermined orientation with respect to the RFID tag 134, a center 214 of the radiofrequency identification tag 134 and a center 216 of the antenna 210 each generally lie on the same (imaginary) line. The collinearity of the center 214 of the radiofrequency identification tag 134 and the center 216 of the antenna 210 and the parallel relationship between the antenna 210 and the radiofrequency identification tag 134 may maximize absorption of RF energy between the radiofrequency identification tag 134 and the antenna 210.

As illustrated in FIG. 3, the antenna 210 can be positioned on the printed circuit board 208 such that the RFID tag 134 is within range 212 of the antenna 210. In advantageous aspects, connections between the connector 100 and the charging port 204 (204A, 204B, 204C, 204D) may be configured such that the RFID tag 134 is within a range 212 of the antenna 210. In advantageous embodiments, the RFID tag 134 can be within a range 212 of the antenna 210 before the connector 100 is fully inserted into the charging port 204. Appreciably, such embodiments may permit an operator to determine whether a suitable catheter 10 (e.g., catheter 10 type, size, whether catheter 10 was used previously) coupled to the connector 100 is being used for a particular procedure.

Figure 4:
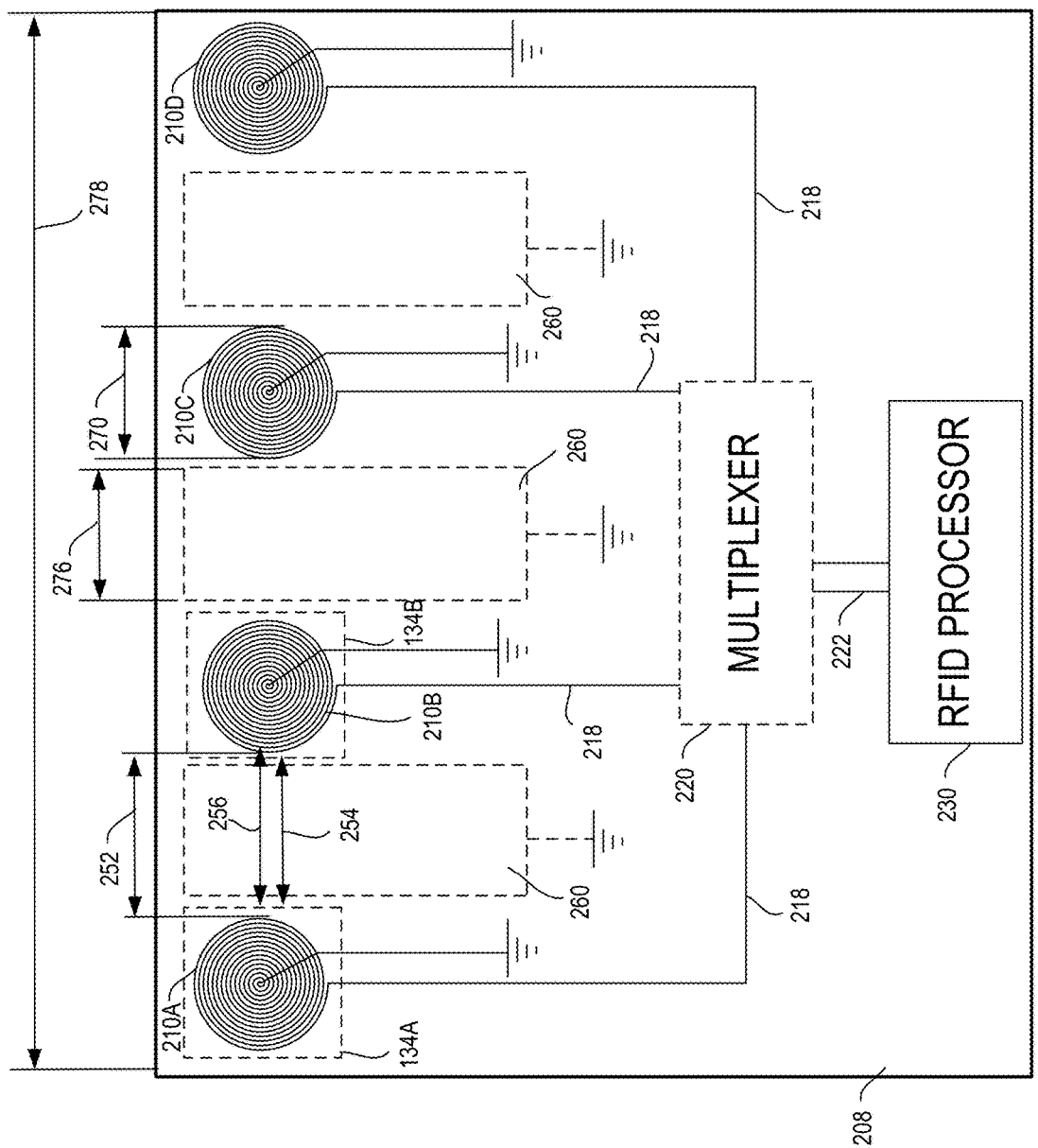
FIG. 4 is a schematic illustrating a printed circuit board with a plurality of antennas positioned thereon.

FIG. 4 illustrates a schematic showing electrical connections between antennas and various electrical components of the charger. In FIG. 4, electrical connections are illustrated by solid lines, while optional components are illustrated by dashed lines. The antenna 210 in the illustrated embodiment is an RF antenna 210. Referencing FIG. 1, four charging ports (204A, 204B, 204C, 204D) are illustrated. Accordingly, in FIG. 4, the charger includes four RF antennas (210A, 210B, 210C, 210D), one each for a corresponding charging port. Additional or fewer charging ports, and additional or fewer antennas are contemplated within the scope of the present disclosure. Each antenna 210 may optionally be in operative communication with a multiplexer 220. Additional electrical circuits 222 may operatively connect the multiplexer 220, and in turn one or more of the antennas with an RFID processor 230. As illustrated in FIG. 4, optionally, one or more shields may be placed in between a pair of antennas.

With continued reference to FIG. 4, in some advantageous embodiments, each of the RF antenna (210A, 210B, 210C, 210D) may be a spiral antenna 210 having a diameter substantially greater than a thickness of the antenna 210. For instance, each antenna 210 may be generally coplanar with each other on a common plane and/or with the printed circuit board 208. In some such advantageous embodiments, the antennas 210 may not protrude substantially above the printed circuit board 208, thereby having a strongly directional radiation emission so as to reduce radiofrequency interaction between adjacent antennas. The common plane may be a plane defined by a portion (e.g., top, bottom, sides, etc.) of each antenna of the plurality of antennas. Further, in certain embodiments, Each antenna of the plurality of antennas lie in the common plane.

In certain embodiments, spiral traces (for instance, made of copper) can be etched on the printed circuit board 208 during manufacturing according to known methods to form the antennas. In advantageous aspects, the RF antenna 210 may be directional. In an exemplary embodiment, the antenna 210 can emit RF signals such that RF signals in a direction generally perpendicular to the plane of the printed circuit board 208 has a first magnitude. Further, the RF signals in directions other than the generally perpendicular direction to the plane of the printed circuit board 208 may be of a second magnitude. In advantageous aspects, the first magnitude can be substantially greater than the second magnitude. For instance, the RF antenna 210 illustrated in FIG. 4 may generally emit RF signals, such that the signal strength in a direction generally outward relative to the plane of FIG. 4 is greater than the signal strength of the RF signals in a direction along the plane of FIG. 4. Referring back to FIG. 3, the outward direction in which the RF signals is emitted by the RF antenna 210 (shown by arrow 242) may generally be oriented toward the RFID tag 134. Accordingly, during insertion of the connector 100 the charging port along the direction 244, the RFID tag 134 may be within range 212 of the antenna 210, and may communicate wirelessly therewith by way of RF signals emitted by the antenna 210. While a spiral antenna 210 is illustrated, other antenna 210 shapes and/or types that minimize radiation of RF energy in directions other than perpendicular to the plane of the circuit board may be used.

According to advantageous aspects of the disclosure, each of the antenna 210 may be configured so as to increase radiofrequency communication with an RFID tag 134 inserted into the corresponding charging port of the antenna 210. Referencing FIGS. 1 and 4, for instance, antenna 210A corresponds to charging port 204A, antenna 210B corresponds to charging port 204B, antenna 210C corresponds to charging port 204C, antenna 210D corresponds to charging port 204D.

In an embodiment, a spacing 250 between an antenna 210A and an RFID tag 134A on a connector 100 when received within a corresponding charging port may be designed so as to increase radiofrequency communication between an antenna 210A and an RFID tag 134A of a connector 100 inserted into a charging port (e.g., charging port 204A). For example, in advantageous aspects, antenna 210A may have radiofrequency communication with an RFID tag 134A provided on a connector 100 inserted into the charging port 204A, while antenna 210B may have radiofrequency communication with an RFID tag 134B provided on a connector 100 inserted into the charging ports 204B. Advantageous aspects of the present disclosure maximize RF energy absorption antenna 210A and RFID tag 134A. Further, RF energy absorption may also be maximized between antenna 210B and RFID tag 134B.

According to certain advantageous aspects, the spacing 250 between antenna 210A and the RFID tag 134A (when inserted at least partially into a charging port 204A) can be less than a first distance 252 between antenna 210A and an adjacent antenna 210B. In illustrative embodiments, the first distance 252 can be a distance between an outermost spiral of two adjacent antennas (e.g., 210A, 210B). In additional or alternative embodiments, the spacing 250 can be less than a second distance 254 between two adjacent tags (e.g., 134A, 134B) that may be housed in connectors inserted into two adjacent charging ports (e.g., 204A, 204B). In further optional embodiments, the spacing 250 can be less than a third distance 256 between the radiofrequency identification tag 134A (e.g., received in charging port 204A) and a nearest antenna (e.g., 210B) adjacent to the corresponding antenna (e.g., 210A). In the illustrated embodiment, while the first distance 252, second distance 254, and third distance 256 are illustrated as being not generally equal to each other, in other embodiments, the first distance 252, second distance 254, and third distance 256 may generally be equal to each other.

In some advantageous embodiments, the spacing 250 can be between greater than about 0 millimeters and less than about 10 millimeters. In some such embodiments, the spacing 250 can be about 4 millimeters. However, other spacing between the RFID tag 134 and the antenna 210 are also contemplated. Such embodiments may permit each antenna 210, when operating as a receiver, to receive RF energy from the RFID tag 134 of a connector 100 inserted into a corresponding charging port, while resulting in less RF energy available for absorption by adjacent antennas. For example, when antenna 210A receives RF energy from the RFID tag 134 of a connector 100 inserted into the charging port 204A, the amount of RF energy available for absorption by antennas 210B, 210C, 210D may be lower than the amount of RF energy available for absorption by antenna 210A (e.g., as a result of spacing 250 being less than distances 252, 254 or 256 between antenna 210A and adjacent antennas 210B, 210C, 210D). Accordingly, RF energy absorption between antenna 210A and RFID tag 134B may be reduced or eliminated. Similarly, RF energy absorption between antenna 210B and RFID tag 134A may be reduced or eliminated. Additionally, antennas 210A and 210B may not communicate with each other according to advantageous aspects of the present disclosure.

In some embodiments, the antennas may be configured so as to reduce radiofrequency communication between each other. As described previously, the antennas may be spiral antennas that radiate generally in a direction perpendicular to the plane of the printed circuit board 208. Accordingly, the antennas may not have significant RF energy in a direction along the plane of the printed circuit board 208, thereby reducing radiofrequency communication between two adjacent antennas. In optional embodiments, one or more ground pads 260 may be placed in between adjacent antennas. In one such optional embodiment, the ground pad 260 can be a metal (e.g., copper) to absorb RF energy that may radiate toward an adjacent antenna 210 so as to minimize radiofrequency communication between adjacent antennas and/or between an RFID tag 134 and antennas other than the corresponding antenna for the RFID tag. In further optional embodiments, one or more shields may be provided to minimize radiofrequency communication between antennas, particularly in instances where a distance between the RFID tag 134 and the antenna 210 exceeds about 10 millimeters. In such cases, the shields may be made of metallized polymer and may extend above a plane of the antennas so as to electrically isolate adjacent charging ports, and thereby minimize radiofrequency communication between adjacent antennas.

In certain embodiments of the disclosure, electrical characteristics of the antennas may be configured so as to increase the amount of RF energy from the RFID tag 134. According to some such embodiments, a frequency of the RF signals emitted by the RFID tag 134 may be between about 14 MHz and 14.5 MHz (for example, 14.4 MHz). Accordingly, the antenna 210 may be configured so as to have a resonant frequency that matches the transmission frequency of the RFID signals. Appreciably, the resonant frequency of an antenna 210 may depend on its inductance. The inductance of the antenna 210 may be chosen so as to result in an antenna 210 resonant at the transmission frequency of the RFID tag 134 (e.g., between about 14 MHz and about 14.5 MHz, for example, about 14.4 MHz).

In additional or alternative embodiments, electrical characteristics of the antenna 210 may also be configured so as to minimize reflections between transmission lines 218 that couple the antennas to transmission side electronics (e.g., multiplexer 220, and additional electrical components). Accordingly, in advantageous aspects, an impedance of an antenna 210 can be matched to an impedance of the transmission side (e.g., electrical lines that couple the antenna 210 to transmission-side electronics such as multiplexer 220). In one example, the antenna 210 may have an impedance of 50 Ohms (by virtue of materials of that form the antenna 210, cross-section of the conductors that form the antenna 210, or the properties of the printed circuit board 208, such as its relative permeability). Accordingly, the electrical lines on the transmission-side electronics that couple the antenna 210 and the transmission-side electronics can be set to 50 Ohms.

In some embodiments, as mentioned previously, the antenna 210 may be a spiral antenna 210. FIG. 5A illustrates an enlarged view of one such antenna 210. Accordingly, in such embodiments, the inductance of the antenna 210, and consequently its resonant frequency may depend on a spiral diameter 270 of the antenna 210, the number of turns, the spacing 272 between each conductor of the spiral and a width 274 of the conductor that forms the spiral shape of the antenna 210. Appreciably, in addition to matching the resonant frequency of the antenna 210 to the transmission frequency of the RFID tag 134, and the impedance of the antenna 210 to the impedance of the transmission line, the antennas may have to be physically accommodated within the overall dimensions of the printed circuit board 208.

In certain advantageous embodiments of the present disclosure, the antenna 210 may be sized and shaped so as to have the antenna 210 resonant frequency equal to transmission frequency of the RFID tag 134, the impedance of the antenna 210 to the impedance of the transmission line, and fit within the space constraints of the printed circuit board 208, while absorbing maximum RF energy from the RFID tag 134. In some such embodiments, the antenna 210 (spiral antenna 210) can have a spiral diameter 270 of between about 2 millimeters and about 10 millimeters. In the illustrated embodiment of FIGS. 5A and 5B, the antenna 210 has a spiral diameter 270 of about 5 millimeters. In some embodiments, a width 274 of the conductor as well as spacing 272 between adjacent turns of the conductor may be between about 0.05 millimeters and about 0.2 millimeters. In the illustrated embodiments of FIGS. 5A and 5B, the conductor width and spacing between adjacent conductors is about 1 millimeter. While a conductor with a generally rectangular cross-section is illustrated in FIG. 5B, appreciably, the conductor can be cylindrical and can have a circular cross-section. Further, the antenna 210 can have between about 15 turns and about 25 turns. In the illustrated embodiment of FIG. 5, the antenna 210 has about 18 turns. Spacing between the antenna 210 and the RFID tag 134, as described previously, can be between about 2 millimeter and about 10 millimeters. In the embodiment illustrated in FIG. 3, the spacing is about 4 millimeters. A width 276 of the grounding pad can be between about 2 millimeters and about 10 millimeters, for example, about 4.5 millimeters, while a width 278 of the printed circuit board 208 can be between about 30 millimeters and about 70 millimeters, for example, about 47 millimeters. As described above, the spacing 250 may be less than distance between adjacent antennas so as to increase the amount of RF energy (emitted by an RFID tag 134) absorbable by a corresponding antenna, while reducing the amount of RF energy (emitted by an RFID tag 134) available for absorption by antennas other than an adjacent antenna. Advantageously, such dimensions result in technical advantages, such as reducing crosstalk between adjacent antennas, matching the resonant frequency of the antenna 210 to the transmission frequency of the RFID tag 134, matching an impedance of the antenna 210 to the impedance of the transmission circuits, and permitting maximum absorption of RF energy emitted by the RFID tag 134 by the antenna 210 while minimizing reflections of RF energy between the transmission side electrical circuits and the antenna 210. Further, such antenna 210 dimensions can also be advantageously housed within a compact sized printed circuit board 208, thereby minimizing space requirements for use with a charger that may, in some cases, have to be positioned in close proximity to (or even on) a patient.

Referring again to FIG. 4, in optional embodiments, a multiplexer 220 is in operative communication with each of the antennas. The multiplexer 220 can be used to read information read by the antennas from the RFID tags sequentially. In alternative embodiments, the information read by the antenna 210 may not necessarily be read in sequence, and instead be read simultaneously. The multiplexer 220 can be a radiofrequency multiplexer having generally the same impedance as the impedance of the antenna and/or transmission lines (e.g., at 50 Ohms).

With continued reference to FIG. 4, in certain aspects, a RFID processor 230 can be in operative communication with the antenna 210 to process information read by the antennas. The RFID processor 230 can be, in some optional embodiments, operatively connected to the multiplexer 220 so as to initiate a sequence in which information is transmitted sequentially by one or more of the plurality of antennas to the RFID processor 230. Alternatively, the transmission lines from the antenna 210 may directly couple the antenna 210 to the RFID processor 230, such that the RFID processor 230 simultaneously receives and processes signals (or information) from the antennas. The RFID processor 230 can be, in some embodiments, application specific integrated circuits (ASICs), microcontrollers, microprocessors, field-programmable gate arrays (FPGAs), or any other appropriate structure capable of receiving and processing data, as well as, circuitry distributed across a network to receive and process data and control system operation as described herein from a remote location. The RFID processor 230 can perform several functions, including, and not limited to, communicate with the antennas to receive information from the RFID tags that are read by the antenna 210, initiate a sequential or simultaneous read of the information, communicate with other on-board or remote processors over a (wired or wireless) network and the like.

Figure 6:
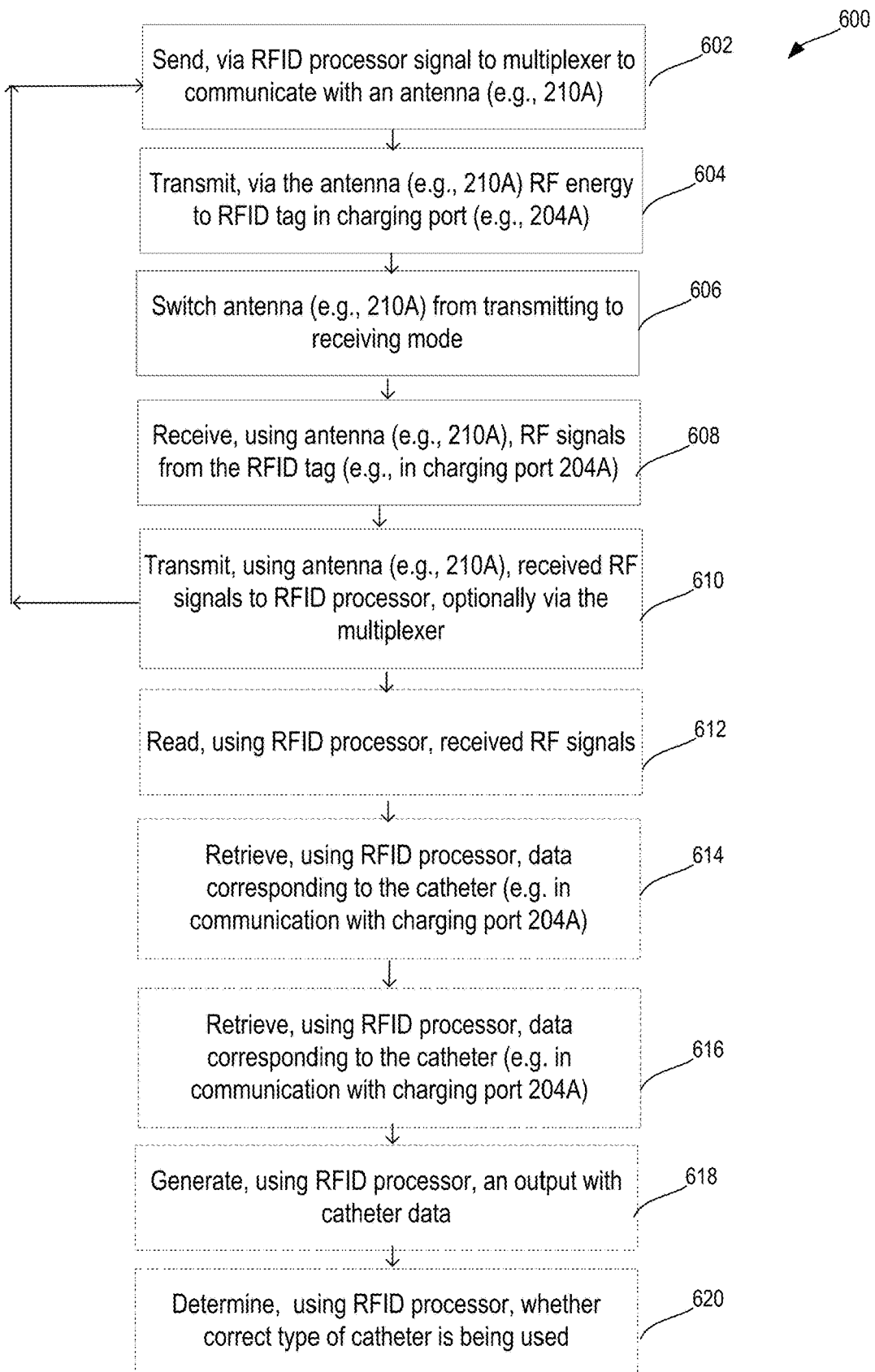
FIG. 6 is a flow chart that illustrates a sequence using which information from a plurality of radiofrequency tags may be read by a radiofrequency processor illustrated in FIG. 4 according to exemplary embodiments of the present disclosure.

FIG. 6 illustrates an algorithm 600 for reading information from a plurality of RFID tags in a sequence according to exemplary embodiments of the present disclosure. At step 602, the RFID processor 230 sends a signal to the multiplexer 220. The signal may, in some embodiments cause the multiplexer 220 to communicate with one of the plurality of antennas. At step 604, in response to the communication and energy transferred between the multiplexer 220 and an antenna 210 (e.g., 210A), the antenna 210 may transmit RF energy to an RFID tag 134 of a connector 100 received in a corresponding port. For example, the antenna 210A may transmit energy to the RFID tag 134 of a connector 100 received in charging port 204A. At step 606, the antenna 210 may switch from a transmitting mode to a receiving mode. At step 608, the antenna 210A may receive RF energy or signals from the RFID tag 134 that includes information that can be used to identify the catheter 10 engaged in the charging port 204A. At step 610, the antenna 210 may transmit the information to the RFID processor 230 (e.g., via the multiplexer 220). Upon receipt of the information, the RFID processor 230 may repeat the process again for the remaining ports (e.g., by reverting to step 602 for another antenna (210B, 210C, 210D)). While FIG. 6 illustrates an algorithm for reading information sequentially, the RFID processor 230 may be in direct communication (e.g., without the multiplexer 220) with the antennas, and can read information transmitted via each antenna 210 simultaneously.

The RFID processor 230 can perform one or more optional steps upon receipt of information transmitted via the antenna 210. As seen in FIG. 6, at optional step 612, the RFID processor 230 can read the information transmitted via the antenna 210. In some embodiments, the information transmitted can be in the form of a unique code. Accordingly, in such embodiments, the RFID processor 230 can, at optional step 614, retrieve (e.g., from a look-up table stored in memory or storage), data for the catheter 10 corresponding to the unique code. For example, the RFID processor 230 may retrieve (at step 616) details such as type of the catheter 10 (e.g., gastrointestinal, urodynamic, anorectal manometry), whether the catheter 10 was previously used, and if so, the patient to whom the catheter 10 corresponds, whether the catheter 10 is new, and if so, the serial number and date of manufacture of the catheter 10 and the like. At step 618, the RFID processor 230 may generate an output that includes one or more of the details of the catheter 10. At optional step 620, the RFID processor 230 may determine whether a correct type of catheter 10 is being used for a correct measurement procedure.

In advantageous aspects, embodiments disclosed herein may be useful in ensuring that the correct type of catheter 10 is used for the correct application. For instance, in some cases, a catheter for measuring bladder pressure may be inserted in a charging port typically used for charging catheters that measure abdominal pressure. In such cases, correctly detecting and identifying the catheter may permit an operator to charge the catheter correctly (e.g., correct charge volumes) for the requisite measurement procedure. Further, the data corresponding to the catheter 10 can also ensure that the charger charges the catheter 10 correctly (e.g., with the correct volume of a pressure transmission medium) for a particular measurement application.

Various examples have been described. These and other examples are within the scope of the following claims.

The invention claimed is:

1. A charger for charging a plurality of pressure sensing catheters, the charger comprising:
 a plurality of charging ports,
 a first charging port of the plurality of charging ports being configured to receive a first connector of a first pressure sensing catheter of the plurality of pressure sensing catheters, the first connector having a first radiofrequency identification tag that has information that is indicative of identifiable information of the first pressure sensing catheter, the first charging port having a first hook engaging surface for engaging a first hook surface of a handle of the first connector at a first side portion of the first charging port and a first antenna at a second side portion of the first charging port, the first side portion of the first charging port being opposite the second side portion of the first charging port,
 a second charging port of the plurality of charging ports being configured to receive a second connector of a second pressure sensing catheter of the plurality of pressure sensing catheters, the second connector having a second radiofrequency identification tag that has information that is indicative of identifiable information of the second pressure sensing catheter, the second charging port having a second hook engaging surface for engaging a first hook surface of a handle of the second connector at a first side portion of the second charging port and a second antenna at a second side portion of the second charging port, the first side portion of the second charging port being opposite the second side portion of the second charging port;
 the first antenna defining a first center axis that intersects the first charging port in a direction perpendicular to a direction in which the first connector is insertable into the first charging port, the first antenna positioned at a different elevation at the first charging port than the first hook engaging surface such that the first connector passes the first center axis of the first antenna before encountering the first hook engaging surface when the first connector is inserted into the first charging port, and the second antenna defining a second center axis that intersects the second charging port in a direction perpendicular to a direction in which the second connector is insertable into the second charging port, the second antenna positioned at a different elevation at the second charging port than the second hook engaging surface such that the second connector passes the second center axis of the second antenna before encountering the second hook engaging surface when the second connector is inserted into the second charging port, the second antenna being adjacent to and generally coplanar with the first antenna on a common plane,
 the first antenna being configured to read the information stored on the first radiofrequency identification tag when the first radiofrequency identification tag is within a range of the first antenna; and the second antenna being configured to read the information stored on the second radiofrequency identification tag when the second radiofrequency identification tag is within a range of the second antenna; such that:
- a spacing between the first radiofrequency identification tag and the first antenna is less than a first distance between the first antenna and the second antenna, or
- the spacing between the first radiofrequency identification tag and the first antenna being less than a second distance between the first radiofrequency identification tag and the second radiofrequency identification tag, or
- the spacing between the first radiofrequency identification tag and the first antenna being less than a third distance between the first radiofrequency identification tag and the second antenna, each of the first antenna and the second antenna having a thickness and a diameter, the thickness being substantially less than the diameter, such that each of the first antenna and the second antenna emits or receives radiofrequency energy in a direction generally perpendicular to the common plane, such that radiofrequency communication between the first radiofrequency tag and the second antenna is minimized.

2. The charger of claim 1, wherein each of the first antenna and the second antenna comprises a spiral antenna having a spiral diameter of between about 2 millimeters and about 10 millimeters, and further comprising a printed circuit board, wherein each spiral antenna is formed on the printed circuit board, each spiral antenna being configured to emit radiofrequency energy in a direction generally perpendicular to a plane of the printed circuit board.

3. The charger of claim 2, further comprising a plurality of grounding pads, each grounding pad being positioned between two adjacent antennas, the grounding pads configured to absorb radiofrequency energy emitted by each antenna in a direction parallel to the plane of the printed circuit board.

4. The charger of claim 2, wherein the spiral antenna comprises a conductor wound in spirals, a width of the conductor forming the spiral antenna between about 0.05 millimeters and about 0.2 millimeters.

5. The charger of claim 2, wherein the spiral antenna has between about 15 spirals and about 25 spirals.

6. The charger of claim 1, wherein each antenna is configured to have a resonant frequency that matches a frequency of transmission of the radiofrequency identification tag.

7. The charger of claim 1, further comprising a radiofrequency identification processor configured to receive, via one or more antennas of the plurality of antennas, information stored on the radiofrequency identification tag, the radiofrequency identification processor being configured to identify the pressure sensing catheter.

8. The charger of claim 7, wherein the radiofrequency identification processor being configured to determine, based on the information received from the radiofrequency identification tag, whether the pressure sensing catheter received in the corresponding charging port is a correct type of catheter for a predetermined measurement procedure.

9. The charger of claim 7, further comprising a multiplexer operatively coupled to the plurality of antennas, the multiplexer being in operative communication with the radiofrequency identification processor.

10. The charger of claim 9, wherein the radiofrequency identification processor is configured to communicate with the multiplexer so as to read information transmitted via the plurality of antennas according to a predetermined sequence.

11. The charger of claim 9, wherein each antenna is electrically connected to the multiplexer by a transmission line, the transmission line having an impedance that equals an impedance of the antenna.

12. The pressure sensing system of claim 1, wherein the spacing between the radiofrequency identification tag and the antenna is less than a distance between the antenna and any antenna of the plurality of antennas other than the antenna.

13. The pressure sensing system of claim 1, wherein the common plane is a plane defined by a portion of each antenna of the plurality of antennas.

14. The pressure sensing system of claim 13, wherein each antenna of the plurality of antennas lie in the common plane.

15. The charger of claim 1, wherein the first radiofrequency identification tag has information that is unique for the first pressure sensing catheter and the second radiofrequency identification tag has information that is unique for the second pressure sensing catheter.

16. A pressure sensing system, comprising:
- a connector connectable to a pressure sensing catheter comprising one or more balloons, the connector having:
  - a handle for grasping the connector at a first side portion of the connector, the handle comprising a first end portion configured to be depressed to cause a second end portion of the handle to engage a hook engaging surface of a charging port via a hook surface of the handle,
  - a tag housing spaced apart from the handle at a second side portion of the connector, the first side portion being opposite the second side portion,
  - a radiofrequency identification tag positioned within the tag housing, the radiofrequency identification tag having information for identifying the pressure sensing catheter;
- a charger for charging the one or more balloons of the pressure sensing catheter, the charger comprising:
  - the charging port for receiving the connector, and
  - an antenna defining a center axis that intersects the charging port in a direction perpendicular to a direction in which the connector is insertable into the charging port, the antenna being configured to read the information stored on the radiofrequency identification tag when the radiofrequency identification tag is within a range of the antenna, the antenna positioned at an opposite side of the charging port from a location at the charging port having the hook engaging surface where the hook surface at the second end portion of the handle engages the charging port, and the antenna positioned at a different elevation at the charging port than the location at the charging port having the hook engaging surface where the hook surface at the second end portion of the handle engages the charging port such that the second end portion of the handle passes the center axis of the antenna before encountering the location at the charging port having the hook engaging surface where the hook surface at the second end portion of the handle engages the charging port when the connector is inserted into the charging port, wherein, when the connector is inserted into the charging port, the radiofrequency identification tag is guided to a predetermined orientation with respect to the antenna, the predetermined orientation orienting the connector such that the second side portion of the connector having the tag housing is closer to the antenna than the first side portion of the connector having the handle, thereby minimizing a spacing between the antenna and the radiofrequency identification tag when the connector is being inserted into the charging port, so as to maximize absorption of radiofrequency energy emitted by the radiofrequency identification tag using the antenna.

17. The pressure sensing system of claim 16, wherein the tag housing is further from an end of the connector that is inserted into the charging port than the second end portion of the handle.

18. The pressure sensing system of claim 16, wherein the spacing between the radiofrequency identification tag and the antenna is such that radiofrequency energy radiated by the radiofrequency identification tag and/or the antenna is generally oriented toward each other.

19. The pressure sensing system of claim 18, wherein the distance between the radiofrequency identification tag and the antenna is between about 2 millimeters and about 10 millimeters, so as to increase absorption of radiofrequency energy emitted by the radiofrequency identification tag using the antenna.

20. The pressure sensing system of claim 16, wherein when at the predetermined orientation, the antenna and the radiofrequency identification tag are generally parallel to each other.

21. The pressure sensing system of claim 16, wherein when at the predetermined orientation, a center of the radiofrequency identification tag and a center of the antenna each generally lie on the same line.

22. The pressure sensing system of claim 16, further comprising:
a second connector connectable to a second pressure sensing catheter, the second connector having a second radiofrequency identification tag positioned thereon, the second radiofrequency identification tag having information for identifying the second pressure sensing catheter;
a second charging port for receiving the second connector; and
a second antenna configured to read the information stored on the second radiofrequency identification tag, when the second radiofrequency identification tag is within a range of the second antenna.

23. The pressure sensing system of claim 22, wherein a spacing between the radiofrequency identification tag and the antenna is less than a distance between the antenna and the second antenna.

24. The pressure sensing system of claim 23, wherein the spacing between the radiofrequency identification tag and the antenna is less than a distance between the radiofrequency identification tag and the second radiofrequency identification tag.

25. The pressure sensing system of claim 24, the spacing between the radiofrequency identification tag and the antenna is less than a distance between the radiofrequency identification tag and the second antenna.

26. The pressure sensing system of claim 16, wherein the handle comprises a first end portion configured to be depressed so as to provide torque to engage the connector with the charging port.

27. The pressure sensing system of claim 26, wherein the handle comprises a second end portion configured to be grasped to guide and insert the connector into the charging port.

28. The pressure sensing system of claim 27, wherein the tag housing is spaced from the first end portion or the second end portion.

29. The pressure sensing system of claim 16, wherein the radiofrequency identification tag has information that is unique for the pressure sensing catheter.

* * * * *